United States Patent [19]
Hirose

[11] Patent Number: 5,721,587
[45] Date of Patent: Feb. 24, 1998

[54] METHOD AND APPARATUS FOR INSPECTING PRODUCT PROCESSED BY TURRET PUNCH PRESS MACHINE

[75] Inventor: Shunzo Hirose, La Mirada, Calif.

[73] Assignee: Amada Mfg America Inc., La Mirada, Calif.

[21] Appl. No.: 499,508

[22] Filed: Jul. 7, 1995

[51] Int. Cl.⁶ ................................................. H04N 7/18
[52] U.S. Cl. .......................................... 348/92; 348/130
[58] Field of Search ............................. 348/86, 87, 88, 348/92, 93, 94, 95, 125, 126, 129, 130, 61; H04N 7/18

[56] References Cited

U.S. PATENT DOCUMENTS

| | | | |
|---|---|---|---|
| 4,555,798 | 11/1985 | Broadbent, Jr. et al. | 348/126 |
| 5,184,217 | 2/1993 | Doering | 348/88 |
| 5,233,536 | 8/1993 | Araki et al. | 348/87 |
| 5,339,103 | 8/1994 | Schmidt et al. | 348/95 |

FOREIGN PATENT DOCUMENTS

| | | |
|---|---|---|
| 3-128133 | 5/1991 | Japan . |
| 5-196423 | 8/1993 | Japan . |

*Primary Examiner*—Bryan S. Tung
*Attorney, Agent, or Firm*—Wigman, Cohen, Leitner & Myers, P.C.

[57] ABSTRACT

In a method of inspecting a product processed by a turret punch press machine, an image sensing apparatus (video camera) (11) is removably fitted in a punch mount hole (5) of an upper turret disk (1) of the turret punch press machine; a product (W) processed on trial by the turret punch press machine and clamped by a work clamping device (23) is fed to an image sensing position of the image sensing apparatus by use of a work locating and feeding mechanism (31, 35, 29, 33) of the turret punch press machine; an image of the processed product is sensed at the image sensing position by the image sensing apparatus; drawing data corresponding to the processed product are inputted; and the image data of the processed product obtained by the image sensing apparatus are compared with the inputted drawing data to discriminate the quality of the processed product quality. Any required image sensing areas on the pressed product can be located and image-sensed for inspection, by use of only the work locating and feeding mechanism of the punch press machine, without applying any punching shock to the video camera.

10 Claims, 4 Drawing Sheets

METHOD AND APPARATUS FOR INSPECTING PRODUCT PROCESSED BY TURRET PUNCH PRESS MACHINE

BACKGROUND OF THE INVENTION

1. Field of the Invention

The present invention relates to a method and apparatus for inspecting a product processed by a turret punch press machine, and more specifically to a method and apparatus for inspecting the quality of a finished pressed product (e.g., acceptance or rejection) by use of an image sensing apparatus.

2. Description of the Related Art

Japanese Published Unexamined Patent Application No. 3-128188 discloses a first example of the inspection method of discriminating the quality result of a pressed product on the basis of image data obtained by sensing an image of a product processed by a turret punch press machine (referred to as a pressed product, hereinafter). In this first inspection method, an image sensing apparatus such as a video camera is mounted on a frame of the turret punch press machine; a pressed product mounted on a worktable and clamped by a work clamp device is moved by a work locating and feeding mechanism so that the pressed product can be image-sensed all over the outer surface thereof; and the quality result of the pressed product is discriminated in accordance with a pattern matching method such that the obtained image data are compared with reference pattern data.

Further, Japanese Published Unexamined Patent Application No. 5-196423 discloses a second example of the inspection method of measuring the processed precision of a pressed product. In this measuring method, after a product has been pressed or punched out, an image sensing apparatus is fitted to a tool mount hole of a turret disk of a turret punch press machine; the pressed product clamped by a work clamp device on a worktable is moved by a work locating and feeding mechanism to an inspection position so that the image of the pressed product can be sensed by the image sensing apparatus; and the pressed precision of the pressed product is measured on the basis of the obtained image data.

In the above-mentioned prior art inspecting method and apparatus, however, there exist some problems as follows: In the case of the first prior art example, a mechanism for mounting the image sensing apparatus is additionally required, and in addition there exists the case where it is impossible to obtain the pressed product image all over the outer surface of the pressed product even if the pressed product is full moved by the work locating and feeding mechanism. This is because the mount position of the image sensing apparatus is usually offset away from the punch-out position by the striker). In addition, since the image sensing apparatus is left mounted on the turret punch press machine during the punching processing, a shock is inevitably applied to the image sensing apparatus of precise electronic instrument whenever work is punched out, with the result that the precision and the life time of image sensing apparatus is subjected to a harmful influence caused by punching shock.

In the case of the second prior art example, on the other hand, although the apparatus can measure the processing precision of the pressed product, it is impossible to discriminate whether the pressed product has been punched out precisely as described on product drawings.

SUMMARY OF THE INVENTION

With these problems in mind, therefore, it is the object of the present invention to provide a method and apparatus for inspecting a product processed by a turret punch press machine, which can discriminate securely whether the pressed produced has been processed precisely as decided by the product drawings in the case of trial punching processing, by sensing all over the surface of the pressed product with the use of only the work locating and feeding mechanism of the turret punch press machine, without applying a punching shock to the image sensing apparatus.

To achieve the above-mentioned object, the present invention provides a method of inspecting a product processed by a turret punch press machine, comprising the steps of: fitting an image sensing apparatus removably in a tool mount hole of a turret disk of the turret punch press machine in the same way as a tool; feeding a product processed by the turret punch press machine and clamped by a work clamping device on a worktable to an image sensing position of the image sensing apparatus by use of a work locating and feeding mechanism of the turret punch press machine; sensing an image of the processed product at the image sensing position by the image sensing apparatus; inputting drawing data corresponding to the processed product; and collating the image data of the processed product obtained by the image sensing apparatus with the inputted drawing data to discriminate processed product quality.

Further, it is preferable that the processed product to be inspected is a product processed on trial, and the image sensing apparatus is indexed to a trial product processed position for inspection.

Further, it is preferable that the method further comprises the steps of: dividing an outer surface of the processed product into a plurality of predetermined image sensing areas; and feeding each of the predetermined image sensing areas of the processed product to the same image sensing position by use of the work locating and feeding mechanism in a predetermined sequence.

Further, the predetermined image sensing areas covers all over the outer surface of the processed product or only punched-out openings of the processed product.

Further, it is preferable that the method further comprises the step of fitting an illumination apparatus removably in a tool mount hole of another turret disk in the same way as a tool so as to be opposed to the image sensing apparatus.

Further, the present invention provides an apparatus for inspecting a product processed by a turret punch press machine, comprising: image sensing means removably fitted in a tool mount hole of a turret disk of the turret punch press machine in the same way as a tool, for sensing at least one predetermined image sensing area of the processed product at an image sensing position of the image sensing apparatus; work locating and feeding means for feeding the predetermined image sensing area of the processed product clamped by a work clamping device on a worktable to the image sensing position of the image sensing apparatus; storing means for storing drawing data of the processed product; and collating means for collating the image data at the predetermined image sensing area of the processed product obtained by said image sensing means with the drawing data stored in said storing means, to discriminate processed product quality.

Further, said image sensing means is a video camera for sensing an image of a predetermined image sensing area determined on an outer surface of the processed product.

Further, said work locating and feeding means comprises:
an X-axis mechanism for feeding the processed product in an X-axis direction; and a Y-axis mechanism for feeding the processed product in a Y-axis direction, to locate the predetermined image sensing area of the processed product at the image sensing position of said image sensing means in cooperation of said X-axis mechanism.

Further, said storing means stores drawing data of the processed product from an automatic programming unit or from a product drawing read through an image scanner.

As described above, in the inspecting method and apparatus for the pressed product according to the present invention, since the image sensing apparatus is fitted to the punch mount hole of the upper turret of the punch press machine and further since any specific image sensing areas of the pressed product can be securely fed and located at the image sensing position of the image sensing apparatus, it is possible to image-sense all over the areas on the pressed product easily by feeding the pressed product by use of only the feeding mechanism of the turret punch press machine, in spite of a relatively simple construction.

Further, since the image sensing apparatus is attached to the turret punch press machine only for inspection of a trial product, for instance, it is possible to prevent the image sensing apparatus from punching shock.

Further, since the whole image sensing area (inspection area) of the pressed product is divided into a plurality of image sensing areas and since the actual image data are compared with drawing data for each divided area in sequence, it is possible to securely specify the inspection area finely and further to store the image data for each image sensing area (each frame), irrespective of the size of the pressed product.

The present invention has been explained in detail with reference to an embodiment. Without being limited thereto, however, it is apparent by those skill in the art that the above-mentioned embodiment can be modified in various ways without departing from the spirit and scope thereof.

DETAILED DESCRIPTION OF THE EMBODIMENTS

An embodiment of the present invention will be described in detail hereinbelow with reference to the attached drawings.

Figure 1:
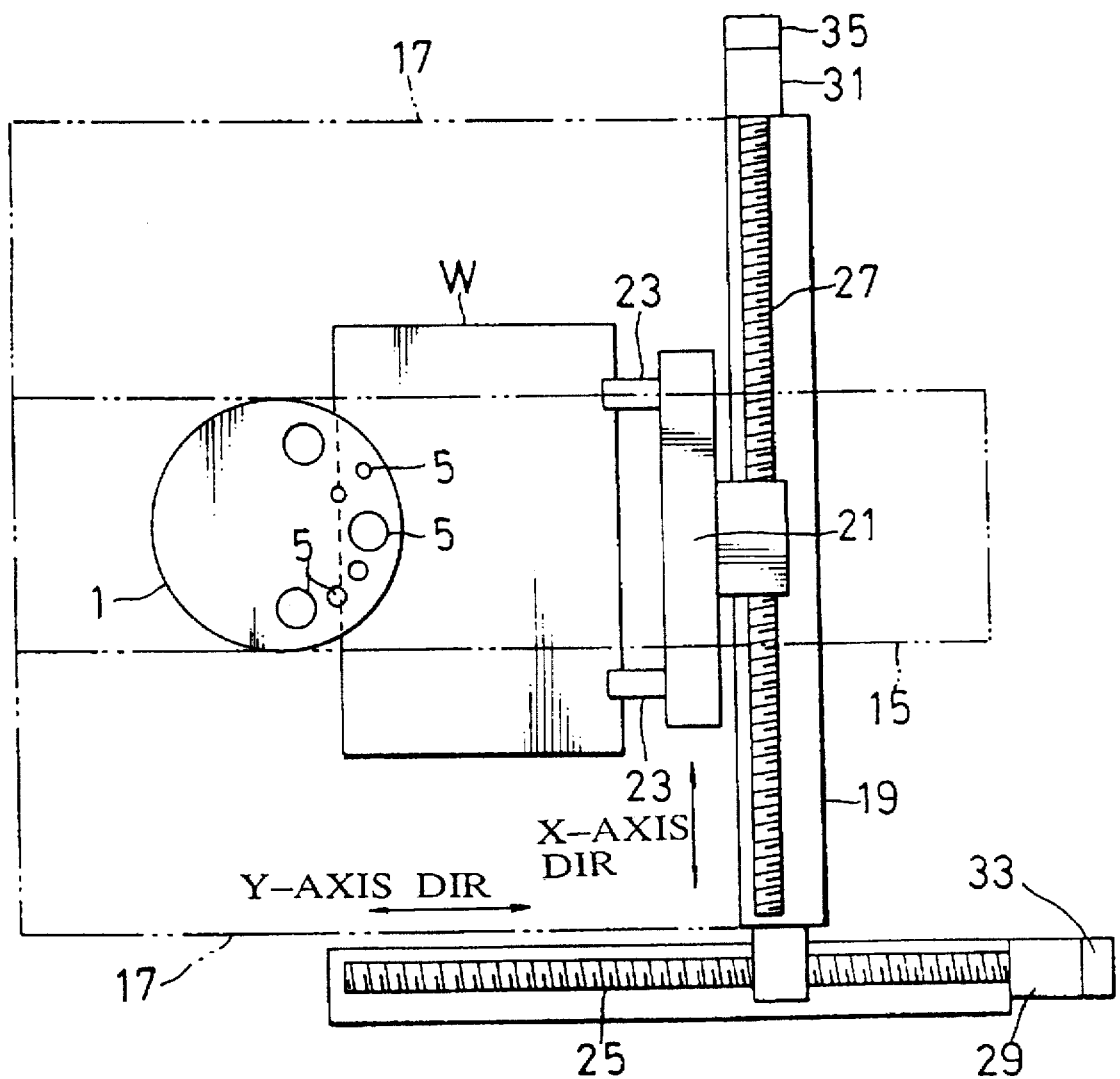
FIG. 1 is a diagrammatical plane view showing an embodiment of the turret punch press machine used to realize the method of inspecting a product processed by the turret punch press machine according to the present invention.
Figure 2:
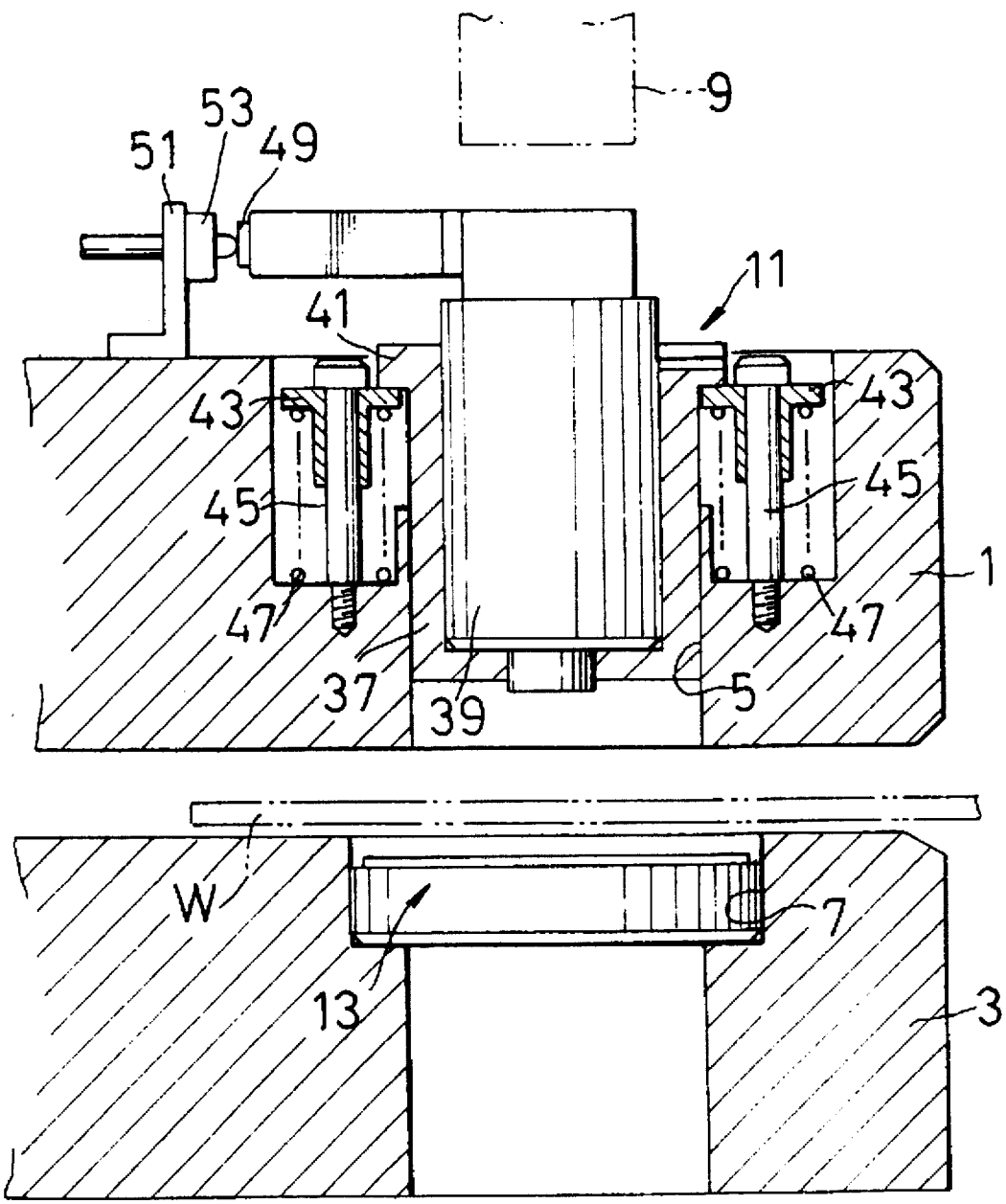
FIG. 2 is a partial longitudinal cross-sectional view showing the image sensing apparatus mounting portion of the turret punch press machine adopted for the method of inspecting a product pressed by the turret punch press machine according to the present invention.

FIGS. 1 and 2 show a turret punch press machine used to inspecting a product processed by a turret punch press machine (referred to as pressed product, hereinafter) according to the present invention.

In FIGS. 1 and 2, the turret punch press machine is provided with an upper rotatable turret disk 1 and a lower rotatable turret disk 3. The upper turret disk 1 is formed with a plurality of punch mount holes 5 and the lower turret disk 3 is formed with a plurality of die mount holes 7. These turret disks 1 and 3 are indexed (rotated for each divided angle) by a known index dividing device in synchronism with each other, so that a pair of the punch mount hole 5 and the die mount hole 7 can be indexed and located at a work punch-out position corresponding to a striker 9.

Into one of the punch mount holes 5 of the upper turret disk 1, an image sensing apparatus 11 is removably fitted. Further, into one of the die mount holes 7 of the lower turret disk 3, an illuminating apparatus 13 is also removably fitted.

On the other hand, on both sides of the center table 15, two (right and left) side tables 17 are provided so as to be movable in the horizontal (Y-axis) direction. Further, a carriage base 19 extending in the vertical (X-axis) direction is fixed to the right and left side tables 17. On the carriage base 19, a carriage 21 is mounted so as to be movable in the X-axis direction. On the carriage 21, a work clamping device 23 for removably clamping work W (e.g., metal sheet) to be pressed or punched out is mounted.

The side tables 17 and the carriage base 19 can be moved in the Y-axis direction together by the rotation of a Y-axis feed screw 25 driven by a Y-axis motor 29, and the carriage 21 and the work clamping device 28 can be moved together in the X-axis direction by the rotation of an X-axis feed screw 27 driven by an X-axis motor 81. Further, a Y-axis position detector (e.g., rotary encoder) 33 is mounted on the Y-axis motor 29, and an X-axis position detector (e.g., rotary encoder) 35 is mounted on the X-axis motor 31 to detect each angular position of the feed screw, respectively.

An image sensing apparatus 11 is composed of a cup-shaped holder 37 removably fitted to the punch mount hole 5 of the upper turret disk 1 in the same way as with the case of the punch and a video camera 39 mounted in the holder 37 so as to be directed in the downward direction. The holder 37 is formed with a flange portion 41 supported by a plurality of lifter retainers 43 of the upper turret disk 1. A plurality of shoulder bolts 45 are fixed to the upper turret disk 1, and the lifter retainers 43 are loosely fitted to the shoulder bolts 45, respectively being urged in the upward direction by a lifter spring 47, respectively.

Further, the image sensing apparatus 11 is provided with a connector 49 for supplying power and transmission signals. Therefore, when the holder 37 is fitted to the punch mount hole 5 of the upper turret disk 1, the connector 49 is automatically connected to another mated connector 53 fixed to the upper turret disk 1 via a connector bracket 51.

The image sensing apparatus 11 can be mounted on the upper turret disk 1 by connecting the two mated connectors 49 and 53 as shown in FIG. 2. Under the condition that the holder 37 of the image sensing apparatus 11 is fitted into the punch mount hole 5 of the upper turret disk 1, a video camera 39 can sense an image of the upper surface of the pressed product W all over the longitudinal and lateral directions thereof, which is located between the upper turret disk 1 and the lower turret disk 3 at the work punch-out position.

Figure 3:
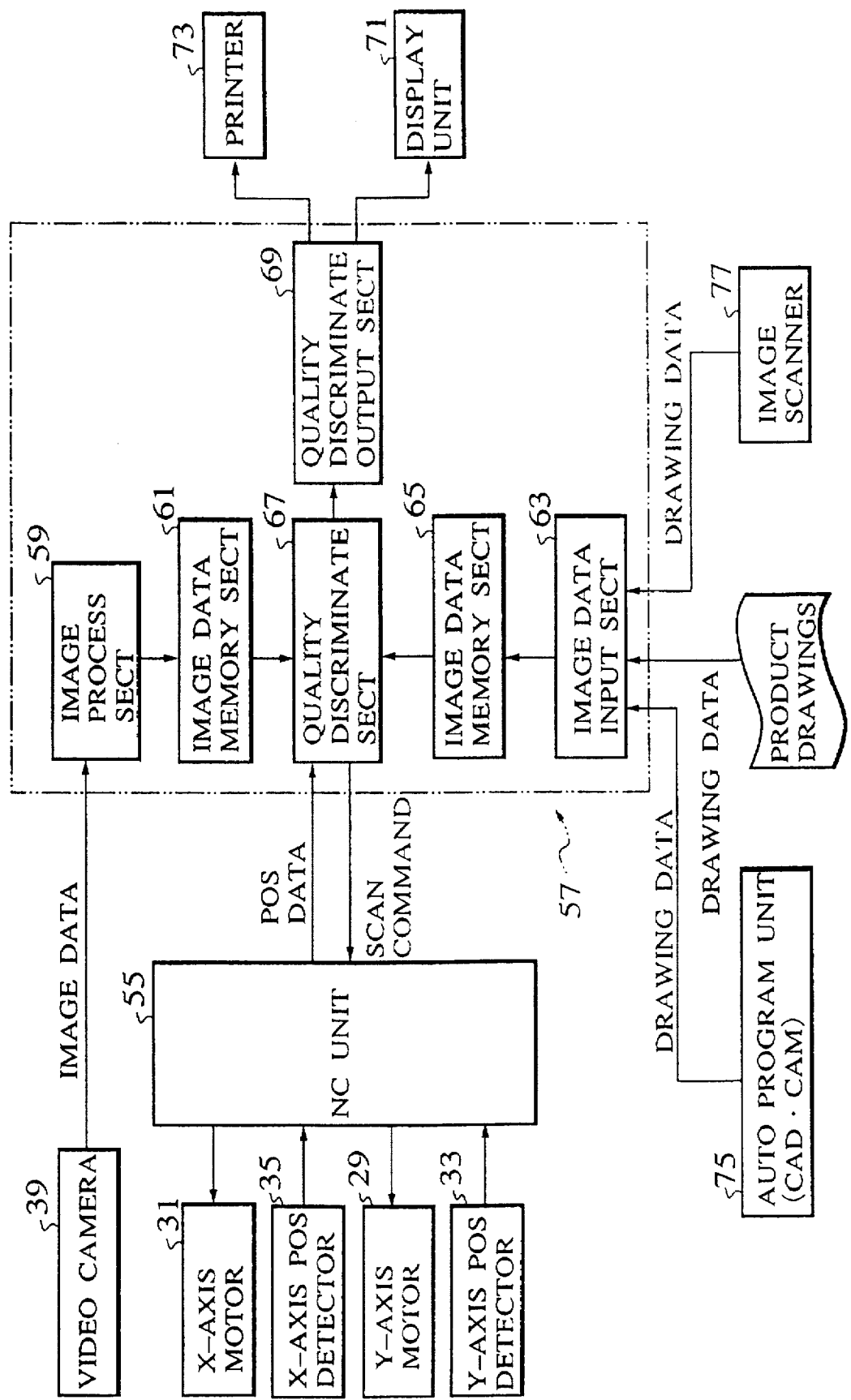
FIG. 3 is a block diagram showing an embodiment of a control system of the turret punch press machine and the pressed product inspecting apparatus according to the present invention.

FIG. 3 shows an embodiment of a control system of an NC turret punch press machine and the pressed product inspecting apparatus. In FIG. 3, an computer NC (numerical control) system 55 outputs a Y-axis motor drive command signal to the Y-axis motor 29 and an X-axis motor drive control signal to the X-axis motor 81, and inputs Y-axis position data (indicative of the position of the carriage base 19) of the Y-axis position detector 38 and X-axis position data (indicative of the position of carriage 21) of the X-axis position detector 35 under positional feedback control.

On the basis of the Y-axis position data and the X-axis position data, the NC system 55 determines a predetermined position (e.g., a punch-out position of the pressed product W), that is, a position to be image-sensed by the video camera 39 on the pressed product W (referred to as image sensing area, hereinafter).

As shown in FIG. 3, the pressed product inspecting apparatus has a data processing unit 57. The data processing unit 57 is composed of an image processing section 59 for processing (e.g., binarization) the inputted image data, an image data memory section (e.g., frame memory) 61 for storing the binarized image data, a drawing data input section 63, a drawing data memory section 65 for storing the inputted drawing data, a product quality discriminate section 67, and a product quality result output section 69 for outputting the discriminated result of the quality discriminate section 67 to a display unit 71 (e.g., CRT) and a printer 73.

The drawing data input section 63 inputs NC programs based upon CAD (computer aided design) data and CAM (computer aided manufacturing) data from an automatic programming unit 75 on line or via a recording medium. Or else, the drawing data input section 63 inputs drawing data read from a product drawing sheet by use of an image scanner 77. In addition, the drawing data input section 63 includes means for executing such a function as to form and input drawing data of the product drawing sheet under control of the CAD program (e.g., a pointing device such as mouse, tablet, etc.).

The quality discriminate section 67 outputs a scanning (positioning) command indicative of a predetermined image sensing area (to be sensed by the video camera 39) on the pressed product W to the NC unit 55, and inputs image position data indicative of the image sensing area on the pressed product W from the NC unit 55. Further, the quality discriminate section 67 reads drawing data at the corresponding image sensing area from the drawing data stored in the drawing data memory section 65 on the basis of the actually inputted image position data, and collates the read drawing data at the corresponding image sensing area with the actual image data stored in the image data memory section 61 in accordance with pattern matching method, for instance in order to discriminate whether a difference rate between the read drawing data and the actual image data is less than a predetermined value or not at each image sensing area; that is, the quality (acceptance or rejection) of the pressed product W.

The above-mentioned inspection of the pressed product W is executed in the following procedure: after the trial punching press has been completed, the image sensing apparatus 11 is fitted to one of the punch mount hole 5 of the upper turret disk 1; the illumination apparatus 13 is fitted to one of the die mount hole 7 of the lower turret disk 3; and the image sensing apparatus 11 and the illumination apparatus 13 are both positioned at the work punch-out position by indexing or rotating the upper and lower turret disks 1 and 3 in synchronism with each other.

Upon completion of the above-mentioned preliminary work, the scanning (positioning) command is outputted from the data processing unit 57 (i.e., the quality discriminate section 67) to the NC unit 55, and further the NC unit 55 outputs the drive command signals to the Y-axis motor 33 and the X-axis motor 35. On the basis of the drive command signals, the side tables 17 and the carriage base 19 are moved in the Y-axis direction, and the carriage 21 is moved in the X-axis direction to move the pressed produce W clamped by the work clamping device 23 in both the Y- and X-axis directions so that a predetermined image sensing area (first image sensing area) on the pressed product W can be located at the image sensing position (the same as the work punch-out position) of the image sensing apparatus 11.

Under these conditions, when the illumination apparatus 13 is activated to illuminate the image sensing area of the pressed product W, so that the illumination light transmits through the punched (pressed) portions of the pressed product W. As a result, it is possible to obtain a strong-contrast image at a predetermined image sensing area of the pressed product W located at the image sensing position of the video camera 39. Here, however, the illumination apparatus 13 disposed on the reverse surface of the pressed product W is not always necessary. That is, the illumination apparatus is used according to the performance of the video camera 39 at need.

The image data at the image sensing area of the pressed product W obtained by the video camera 39 are processed (e.g., binarized) by the image data processing section 59 of the data processing unit 57, and then stored in the image memory section 61. On the basis of the image data signals, the quality discriminate section 67 of the data processing unit 57 inputs the image position data for specifying the image sensing area of the pressed product W, reads the drawing data at the corresponding image sensing area from the drawing data previously stored in the drawing data memory section 65 on the basis of the image position data, and collates the actual image data stored in the image data memory section 61 with the read drawing data at the corresponding image sensing area in accordance with a pattern matching, for instance to discriminate whether a difference between the actual image data and the drawing data is less than a predetermined value, that is, the quality of the pressed product W. The obtained quality result is outputted to the display 71 through the quality result output section 69 for display or to the printer 73 for printing out at need.

Upon completion of the image sensing of the pressed product W at the first image sending area, the data processing unit 57 (i.e., the quality discriminate section 67) outputs another scanning (positioning) command to the NC unit 55, so that the NC unit 55 outputs the motor drive command signals to the Y-axis motor 33 and the X-axis motor 35, respectively to move the side tables 17 and the carriage base 19 in the Y-axis direction and the carriage 21 in the X-axis direction. As a result, the pressed product W clamped by the work clamping device 23 is moved in both the Y- and X-axis directions to locate the second image sensing area of the pressed product W at the image sensing position of the image sensing apparatus 11. Therefore, the second image sensing area on the pressed product W can be image-sensed by the image sensing apparatus 11. After that, in the same way as already explained, the NC unit 55 reads the drawing data at the second corresponding image sensing area from the drawing data previously stored in the drawing data memory section 65, and discriminates the quality of the pressed product W on the basis of a difference between the actual image data and the stored drawing data for each image area.

Figures 4, 5:
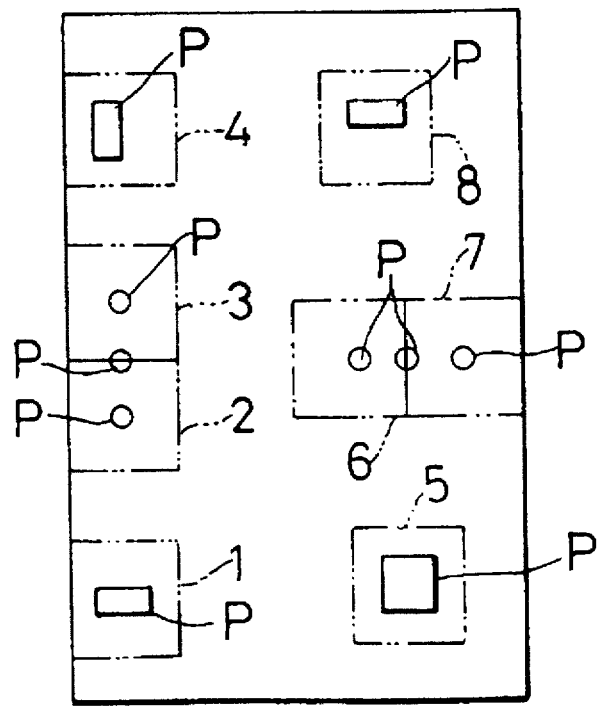
FIG. 4 is a plane view showing an example of the image sensing areas of the pressed product in the method of inspecting a product pressed by the turret punch press machine according to the present invention.
FIG. 5 is a plane view showing another example of the image sensing areas of the pressed product in the method according to the present invention.

FIG. 4 shows an example of the image sending areas of the pressed product W, which extends all over the pressed product W. In FIG. 4, the surface of the pressed product W is divided into 24 image sensing areas, and these image sensing areas are image-sensed in the order of the numbers from 1 to 24.

When the image sensing areas by the image sensing apparatus 11 extend all over the surface of the pressed product W as shown in FIG. 4, it is possible to detect or inspect various inspection items such as an erroneous mounting of the punch and die on the punch mount hole 5 of the upper turret disk 1 or on the die mount hole 7 of the lower turret disk 3, defective punching due to erroneous die designation by the NC processing program, erroneous punching positions by the NC processing program, etc.

FIG. 5 shows another example of the image sensing areas, in which only the punched-out areas of the pressed product W are selected or extracted. In FIG. 5, the image areas are image-sensed in the order of the numbers from 1 to 8, and P designates holes (apertures) punched out by the turret punch press machine. In this example, it is possible to reduce the number of image sensing areas to be sensed by the image sensing apparatus 11, so that although the defective punching due to erroneous punching position designation by the NC program can not be detected, the inspection time can be shortened.

Further, the punched areas on the pressed product W can be extracted automatically on the basis of the data processing of the computer, because the punching positions are already described in the NC program.

As described above, in the inspecting method and apparatus for the pressed product according to the present invention, since the image sensing apparatus is fitted to the punch mount hole of the upper turret of the punch press machine and further since any specific image sensing areas of the pressed product can be securely fed and located at the image sensing position of the image sensing apparatus, it is possible to image-sense all over the areas on the pressed product easily by feeding the pressed product by use of only the feeding mechanism of the turret punch press machine, in spite of a relatively simple construction.

Further, since the image sensing apparatus is attached to the turret punch press machine only for inspection of a trial product, for instance, it is possible to prevent the image sensing apparatus from punching shock.

Further, since the whole image sensing area (inspection area) of the pressed product is divided into a plurality of image sensing areas and since the actual image data are compared with drawing data for each divided area in sequence, it is possible to securely specify the inspection area finely and further to store the image data for each image sensing area (each frame), irrespective of the size of the pressed product.

The present invention has been explained in detail with reference to an embodiment. Without being limited thereto, however, it is apparent by those skill in the art that the above-mentioned embodiment can be modified in various ways without departing from the spirit and scope thereof.

What is claimed is:

1. A method of inspecting a product processed by a turret punch press machine, comprising the steps of:

fitting an image sensing apparatus removably in a tool mount hole of a turret disk of the turret punch press machine in the same way as a tool;

fitting an illustration apparatus removably in a tool mount hole of another turret disk of the turret punch press machine in thew same way as a tool, so as to be opposed to the image sensing apparatus;

feeding a product processed by the turret punch press machine and clamped by a work clamping device on a work table to an image sensing position of the image sensing apparatus by use of work locating and feeding mechanism of the turret punch press machine;

sensing an image of the processed product at the image sensing position by the image sensing apparatus;

inputting drawing data corresponding to the processed product; and collating the image data of the processed product obtained by the image sensing apparatus with the inputted drawing data to discriminate processed product quality.

2. The method of inspecting a product processed by a turret punch press machine of claim 1, wherein the processed product to be inspected is a product processed on trial, and the image sensing apparatus is indexed to a trial product processed position for inspection.

3. The method of inspecting a product processed by a turret punch press machine of claim 1, which further comprises the steps of:

dividing an outer surface of the processed product into a plurality of predetermined image sensing areas; and feeding each of the predetermined image sensing areas of the processed product to the same image sensing position by use of the work locating and feeding mechanism in a predetermined sequence.

4. The method of inspecting a product processed by a turret punch press machine of claim 3, wherein the predetermined image sensing areas covers all over the outer surface of the processed product.

5. The method of inspecting a product processed by a turret punch press machine of claim 3, wherein the predetermined image sensing areas covers only punched-out openings of the processed product.

6. An apparatus for inspecting a product processed by a turret punch press machine, comprising:

image sensing means removably fitted in a tool mount hole of a turret disk of the turret punch press machine in the same way as a tool, for sensing at least one predetermined image sensing area of the processed product at an image sensing position of the image sensing apparatus;

illuminating means removably fitted in a tool mount hole of another turret disk of the turret punch press machine in the same way as a tool so as to be opposed to the image sensing apparatus, for illuminating the predetermined image sensing area of the processed product from a back side thereof;

work locating and feeding means for feeding the predetermined image sensing area of the processed product clamped by a work clamping device on a worktable to the image sensing position of the image sensing apparatus;

storing means for storing drawing data of the processed product; and collating means for collating the image data at the predetermined image sensing area of the processed product obtained by said image sensing means with the drawing data stored in said storing means, to discriminate processed product quality.

7. The apparatus for inspecting a product processed by a turret punch press machine of claim 6, wherein said image sensing means is a video camera for sensing an image of a predetermined image sensing area determined on an outer surface of the processed product.

8. The apparatus for inspecting a product processed by a turret punch press machine of claim 6, wherein said work locating and feeding means comprises:
- an X-axis mechanism for feeding the processed product in an X-axis direction; and
- a Y-axis mechanism for feeding the processed product in a Y-axis direction, to locate the predetermined image sensing area of the processed product at the image sensing position of said image sensing means in cooperation of said X-axis mechanism.

9. The apparatus for inspecting a product processed by a turret punch press machine of claim 6, wherein said storing means stores drawing data of the processed product from an automatic programming unit.

10. The apparatus for inspecting a product processed by a turret punch press machine of claim 6, wherein said storing means stores drawing data of the processed product from a product drawing read through an image scanner.

* * * * *